United States Patent
Helkowski et al.

(10) Patent No.: US 9,259,348 B2
(45) Date of Patent: Feb. 16, 2016

(54) TRANSATRIAL PATIENT TEMPERATURE CONTROL CATHETER

(75) Inventors: Richard A. Helkowski, Redwood City, CA (US); Jeremy T. Dabrowiak, Redwood City, CA (US); Alex L. Lim, Santa Clara, CA (US); Venkata Vishnu Gurukula, Mountain View, CA (US)

(73) Assignee: Zoll Circulation, Inc., San Jose, CA (US)

( * ) Notice: Subject to any disclaimer, the term of this patent is extended or adjusted under 35 U.S.C. 154(b) by 973 days.

(21) Appl. No.: 13/247,044

(22) Filed: Sep. 28, 2011

(65) Prior Publication Data

US 2013/0079858 A1    Mar. 28, 2013

(51) Int. Cl.
*A61F 7/12* (2006.01)
*A61F 7/00* (2006.01)

(52) U.S. Cl.
CPC . *A61F 7/12* (2013.01); *A61F 7/123* (2013.01); *A61F 2007/0054* (2013.01); *A61F 2007/0096* (2013.01); *A61F 2007/126* (2013.01)

(58) Field of Classification Search
CPC ... A61F 7/12; A61F 7/123; A61F 2007/0095; A61F 2007/0096; A61F 2007/126
USPC .................................................. 607/106, 113
See application file for complete search history.

(56) References Cited

U.S. PATENT DOCUMENTS

| | | | |
|---|---|---|---|
| 1,459,112 A | 6/1923 | Mehl | |
| 1,857,031 A | 5/1932 | Schaffer | |
| 2,663,030 A | 12/1953 | Dahlberg | |
| 2,673,987 A | 4/1954 | Upshaw et al. | |
| 3,225,191 A | 12/1965 | Calhoun | |
| 3,369,549 A | 2/1968 | Armao | |
| 3,425,419 A | 2/1969 | Actis Dato | |
| 3,504,674 A | 4/1970 | Swenson | |
| 3,726,269 A | 4/1973 | Webster, Jr. | |
| 3,744,555 A | 7/1973 | Fletcher et al. | |
| 3,751,077 A | 8/1973 | Hiszpanski | |
| 3,937,224 A | 2/1976 | Uecker | |
| 3,945,063 A | 3/1976 | Matsuura | |
| 4,038,519 A | 7/1977 | Foucras | |

(Continued)

FOREIGN PATENT DOCUMENTS

DE    19531935    2/1997
GB    2040169    8/1980

(Continued)

OTHER PUBLICATIONS

F.W. Behmann, E. Bontke, "Die Regelung der Wärmebildung bei künstlicher Hypothermie", Pflügers Archiv, Bd. 266, S. 408-421 (1958).

(Continued)

*Primary Examiner* — Kaitlyn Smith
(74) *Attorney, Agent, or Firm* — John L. Rogitz

(57) ABSTRACT

A transatrial intravascular temperature management catheter has a lower heat exchange segment positionable in the inferior vena cava and an upper heat exchange segment positionable in the superior vane cava, with a connecting segment lying between the two and positionable in the right atrium. A temperature sensor on the distal tip of the upper heat exchange segment provides accurate core body temperature signals for feedback purposes since the blood flowing past the sensor has not yet reached the heat exchange segment.

19 Claims, 3 Drawing Sheets

(56) References Cited

U.S. PATENT DOCUMENTS

| | | |
|---|---|---|
| 4,065,264 A | 12/1977 | Lewin |
| 4,103,511 A | 8/1978 | Kress et al. |
| 4,126,132 A | 11/1978 | Portner et al. |
| 4,153,048 A | 5/1979 | Magrini |
| 4,173,228 A | 11/1979 | Van Steenwyk et al. |
| 4,181,132 A | 1/1980 | Parks |
| 4,298,006 A | 11/1981 | Parks |
| 4,459,468 A | 7/1984 | Bailey |
| 4,532,414 A | 7/1985 | Shah et al. |
| 4,554,793 A | 11/1985 | Harding, Jr. |
| 4,581,017 A | 4/1986 | Sahota |
| 4,638,436 A | 1/1987 | Badger et al. |
| 4,653,987 A | 3/1987 | Tsuji et al. |
| 4,661,094 A | 4/1987 | Simpson |
| 4,665,391 A | 5/1987 | Spani |
| 4,672,962 A | 6/1987 | Hershenson |
| 4,754,752 A | 7/1988 | Ginsburg et al. |
| 4,787,388 A | 11/1988 | Hofmann |
| 4,813,855 A | 3/1989 | Leveen et al. |
| 4,849,196 A | 7/1989 | Yamada et al. |
| 4,852,567 A | 8/1989 | Sinofsky |
| 4,860,744 A | 8/1989 | Johnson et al. |
| 4,906,237 A | 3/1990 | Johansson et al. |
| 4,941,475 A | 7/1990 | Williams et al. |
| 5,092,841 A | 3/1992 | Spears |
| 5,103,360 A | 4/1992 | Maeda |
| 5,106,360 A | 4/1992 | Ishiwara et al. |
| 5,174,299 A * | 12/1992 | Nelson .......................... 600/505 |
| 5,192,274 A | 3/1993 | Bierman |
| 5,195,965 A | 3/1993 | Shantha |
| 5,211,631 A | 5/1993 | Sheaff |
| 5,269,758 A | 12/1993 | Taheri |
| 5,281,215 A | 1/1994 | Milder |
| 5,304,214 A | 4/1994 | DeFord et al. |
| 5,334,346 A | 8/1994 | Kim et al. |
| 5,342,301 A | 8/1994 | Saab |
| 5,344,436 A | 9/1994 | Fontenot et al. |
| 5,370,675 A | 12/1994 | Edwards et al. |
| 5,383,856 A | 1/1995 | Bersin |
| 5,403,281 A | 4/1995 | O'Neill et al. |
| 5,433,740 A | 7/1995 | Yamaguchi |
| 5,437,673 A | 8/1995 | Baust et al. |
| 5,458,639 A | 10/1995 | Tsukashima et al. |
| 5,486,207 A | 1/1996 | Mahawili |
| 5,486,208 A | 1/1996 | Ginsburg |
| 5,507,792 A | 4/1996 | Mason et al. |
| 5,531,714 A | 7/1996 | Dahn et al. |
| 5,531,776 A | 7/1996 | Ward et al. |
| 5,542,928 A | 8/1996 | Evans et al. |
| 5,624,392 A | 4/1997 | Saab |
| 5,634,907 A | 6/1997 | Rani et al. |
| 5,676,670 A | 10/1997 | Kim |
| 5,701,905 A | 12/1997 | Esch |
| 5,709,564 A | 1/1998 | Yamada et al. |
| 5,709,654 A | 1/1998 | Klatz et al. |
| 5,716,386 A | 2/1998 | Ward et al. |
| 5,730,720 A | 3/1998 | Sites et al. |
| 5,733,319 A | 3/1998 | Neilson et al. |
| 5,737,782 A | 4/1998 | Matsuura et al. |
| 5,776,079 A | 7/1998 | Cope et al. |
| 5,788,647 A | 8/1998 | Eggers |
| 5,837,003 A | 11/1998 | Ginsburg |
| 5,862,675 A | 1/1999 | Scaringe et al. |
| 5,895,418 A | 4/1999 | Saringer |
| 5,908,407 A | 6/1999 | Frazee et al. |
| 5,957,963 A | 9/1999 | Dobak, III |
| 5,971,935 A * | 10/1999 | Higgins et al. .................. 600/526 |
| 5,980,561 A | 11/1999 | Kolen et al. |
| 6,019,783 A | 2/2000 | Philips et al. |
| 6,042,559 A | 3/2000 | Dobak, III |
| 6,051,019 A | 4/2000 | Dobak, III |
| 6,059,825 A | 5/2000 | Hobbs et al. |
| 6,096,068 A | 8/2000 | Dobak, III et al. |
| 6,110,139 A | 8/2000 | Loubser |
| 6,117,065 A | 9/2000 | Hastings et al. |
| 6,117,105 A | 9/2000 | Bresnaham et al. |
| 6,124,452 A | 9/2000 | Di Magno |
| 6,126,684 A | 10/2000 | Gobin et al. |
| 6,146,141 A | 11/2000 | Schumann |
| 6,146,411 A | 11/2000 | Noda et al. |
| 6,148,634 A | 11/2000 | Sherwood |
| 6,149,670 A | 11/2000 | Worthen et al. |
| 6,149,677 A | 11/2000 | Dobak, III |
| 6,231,594 B1 | 5/2001 | Dae |
| 6,283,940 B1 | 9/2001 | Mulholland |
| 6,299,599 B1 | 10/2001 | Pham et al. |
| 6,338,727 B1 | 1/2002 | Noda et al. |
| 6,383,144 B1 | 5/2002 | Mooney et al. |
| 6,383,172 B1 * | 5/2002 | Barbut .......................... 604/509 |
| 6,383,210 B1 * | 5/2002 | Magers et al. ................ 607/105 |
| 6,409,747 B1 | 6/2002 | Gobin et al. |
| 6,416,533 B1 | 7/2002 | Gobin et al. |
| 6,428,563 B1 | 8/2002 | Keller |
| 6,450,990 B1 | 9/2002 | Walker et al. |
| 6,464,716 B1 | 10/2002 | Dobak, III et al. |
| 6,520,933 B1 * | 2/2003 | Evans et al. ............... 604/103.07 |
| 6,527,798 B2 | 3/2003 | Ginsburg et al. |
| 6,530,946 B1 | 3/2003 | Noda et al. |
| 6,544,282 B1 | 4/2003 | Dae et al. |
| 6,551,309 B1 | 4/2003 | Le Pivert |
| 6,554,791 B1 | 4/2003 | Cartledge et al. |
| 6,582,398 B1 * | 6/2003 | Worthen et al. ................ 604/113 |
| 6,605,106 B2 | 8/2003 | Schwartz |
| 6,607,517 B1 * | 8/2003 | Dae et al. ...................... 604/500 |
| 6,610,083 B2 | 8/2003 | Keller et al. |
| 6,620,187 B2 | 9/2003 | Carson et al. |
| 6,620,188 B1 | 9/2003 | Ginsburg et al. |
| 6,624,679 B2 | 9/2003 | Tomaivolo et al. |
| 6,635,076 B1 | 10/2003 | Ginsburg |
| 6,679,906 B2 | 1/2004 | Hammack et al. |
| 6,685,733 B1 | 2/2004 | Dae et al. |
| 6,706,060 B2 | 3/2004 | Tzeng et al. |
| 6,716,188 B2 | 4/2004 | Noda et al. |
| 6,719,723 B2 | 4/2004 | Werneth |
| 6,719,779 B2 | 4/2004 | Daoud |
| 6,726,653 B2 | 4/2004 | Noda et al. |
| 6,733,517 B1 | 5/2004 | Collins |
| 6,740,109 B2 | 5/2004 | Dobak, III |
| 6,799,342 B1 | 10/2004 | Jarmon |
| 6,843,800 B1 | 1/2005 | Dobak, III |
| 6,887,263 B2 | 5/2005 | Bleam et al. |
| 6,893,419 B2 | 5/2005 | Noda et al. |
| 6,969,399 B2 | 11/2005 | Schock et al. |
| 7,510,569 B2 | 3/2009 | Dae et al. |
| 7,577,478 B1 * | 8/2009 | Kroll et al. ........................ 607/6 |
| 7,666,215 B2 | 2/2010 | Callister et al. |
| 7,822,485 B2 | 10/2010 | Collins |
| 7,846,193 B2 | 12/2010 | Dae et al. |
| 7,857,781 B2 | 12/2010 | Noda et al. |
| 7,892,270 B2 * | 2/2011 | Winter .......................... 607/105 |
| 8,105,262 B2 | 1/2012 | Noda et al. |
| 8,105,263 B2 | 1/2012 | Noda et al. |
| 8,105,264 B2 | 1/2012 | Noda et al. |
| 8,109,894 B2 | 2/2012 | Noda et al. |
| 2001/0010011 A1 * | 7/2001 | Aliberto et al. ................ 607/105 |
| 2001/0031946 A1 | 10/2001 | Walker et al. |
| 2001/0041923 A1 * | 11/2001 | Dobak, III ..................... 607/108 |
| 2001/0047196 A1 | 11/2001 | Ginsburg et al. |
| 2002/0013569 A1 | 1/2002 | Sterman et al. |
| 2002/0022823 A1 | 2/2002 | Luo et al. |
| 2002/0045925 A1 | 4/2002 | Keller et al. |
| 2002/0111584 A1 * | 8/2002 | Walker et al. ................. 604/113 |
| 2002/0111616 A1 * | 8/2002 | Dea et al. ......................... 606/41 |
| 2002/0120314 A1 * | 8/2002 | Evans et al. ..................... 607/96 |
| 2002/0145525 A1 | 10/2002 | Friedman et al. |
| 2002/0183692 A1 | 12/2002 | Callister |
| 2002/0198579 A1 | 12/2002 | Khanna |
| 2003/0130651 A1 * | 7/2003 | Lennox .......................... 606/21 |
| 2003/0236496 A1 | 12/2003 | Samson et al. |
| 2004/0073280 A1 | 4/2004 | Dae et al. |
| 2004/0089058 A1 | 5/2004 | De Haan et al. |
| 2004/0102825 A1 | 5/2004 | Daoud |
| 2004/0210231 A1 | 10/2004 | Boucher et al. |
| 2005/0156744 A1 | 7/2005 | Pires |

(56) References Cited

U.S. PATENT DOCUMENTS

| | | | |
|---|---|---|---|
| 2007/0007640 | A1 | 1/2007 | Harnden et al. |
| 2007/0043409 | A1 | 2/2007 | Brian, III et al. |
| 2007/0076401 | A1 | 4/2007 | Carrez et al. |
| 2008/0071337 | A1 | 3/2008 | Dobak, III et al. |
| 2008/0119788 | A1 | 5/2008 | Winter |
| 2009/0254161 | A1 | 10/2009 | Dae et al. |
| 2010/0241201 | A1* | 9/2010 | Noda et al. ............ 607/113 |

FOREIGN PATENT DOCUMENTS

| | | |
|---|---|---|
| GB | 1183185 | 2/1985 |
| GB | 2212262 | 7/1989 |
| GB | 2383828 | 7/2003 |
| JP | 09-215754 | 8/1997 |
| JP | 10-0127777 | 5/1998 |
| JP | 10-305103 | 11/1998 |
| JP | 2002542892 | 12/2002 |
| JP | 2003175070 | 6/2003 |
| JP | 2010137067 | 6/2010 |
| WO | 9001682 | 2/1990 |
| WO | 9304727 | 3/1993 |
| WO | 9400177 | 1/1994 |
| WO | 9401177 | 1/1994 |
| WO | 9725011 | 7/1997 |
| WO | 9824491 | 6/1998 |
| WO | 9840017 | 9/1998 |
| WO | 0010494 | 3/2000 |
| WO | 0113809 | 3/2001 |
| WO | 0164146 | 9/2001 |
| WO | 0176517 | 10/2001 |
| WO | 0183001 | 11/2001 |
| WO | 2002036180 A2 | 5/2002 |
| WO | 2004023982 A2 | 3/2004 |
| WO | 2004069304 A2 | 8/2004 |
| WO | 2004075949 A2 | 9/2004 |

OTHER PUBLICATIONS

F.W. Behmann, E. Bontke, "Intravasale Kühlung", Pffügers Archiv, Bd. 263, S. 145-165 (1956).

Wilhelm Behringer, Stephan Prueckner, Rainer Kenter, Samuel A. Tisherman, Ann Radovsky, Robert Clark, S. William Stezoski, Heremy Henchir, Edwin Klein, Peter Safar, "Rapid Hypothermic Aortic Flush Can Achieve Survival without Brain Damage after 30 Minutes Cardiac Arrest in Dogs", anesthesiology, V. 93, No. 6, Dec. 2000.

Dorraine Day Watts, Arthur Trask, Karen Soeken, Philip Predue, Sheilah Dols, Christopher Kaufman; "Hypothermic Coagulopathy in trauma: Effect of Varying levels of Hypothermia on Enzyme Speed, Platelet Function, and Fibrinolytic Activity". The Journal of Trauma: Injury, Infection, and Critical Care, Vo. 44, No. 5 (1998).

Mark A. Saab, "Multi-Lumen Heat Transfer Catheter System", file history of pending U.S. Appl. No. 12/924,933, filed Oct. 8, 2010.

David J. Scott, Ben F. Brian, Lloyd F. Wright, Leo A. Chin, Edward W. Hollmen, Saniel W. Seegars, Mark A. Logan, "Apparatus and Method for Providing Enhanced Heat Transfer from a Body", file history of pending U.S. Appl. No. 12/897,637, filed Oct. 4, 2010.

Timothy R. MacHold, Nicole Denise Bloom, Alex T. Roth, Dave J. Scott, Jose Alejandro, Edward A. Oliver, "Method and Apparatus for Regional and Whole Body Temperature Modification", file history of pending U.S. Appl. No. 13/101,000, filed May 4, 2011.

Timothy R. MacHold, Nicole Denise Bloom, Alex T. Roth, Dave J. Scott, Jose Alejandro, Edward A. Oliver, "Method and Apparatus for Regional and Whole Body Temperature Modification", file history of pending U.S. Appl. No. 13/101,036, filed May 4, 2011.

Timothy R. MacHold, Wade A. Keller, Alex T. Roth, Nicole Denise Bloom, "Method and System for Control of a Patient's Body Temperature by Way of a Transluminally Insertable Heat Exchange Catheter", file history of pending U.S. Appl. No. 13/161,648, filed Jun. 20, 2011.

* cited by examiner

TRANSATRIAL PATIENT TEMPERATURE CONTROL CATHETER

FIELD OF THE INVENTION

The present application relates generally to patient temperature control systems.

BACKGROUND OF THE INVENTION

It has been discovered that the medical outcome for a patient suffering from severe brain trauma or from ischemia caused by stroke or heart attack or cardiac arrest is improved if the patient is cooled below normal body temperature (37° C.). Furthermore, it is also accepted that for such patients, it is important to prevent hyperthermia (fever) even if it is decided not to induce hypothermia. Moreover, in certain applications such as post-CABG surgery, it might be desirable to rewarm a hypothermic patient.

As recognized by the present application, the above-mentioned advantages in regulating temperature can be realized by cooling or heating the patient's entire body using a closed loop heat exchange catheter placed in the patient's venous system and circulating a working fluid such as saline through the catheter, heating or cooling the working fluid as appropriate in an external heat exchanger that is connected to the catheter. The following U.S. patents, all of which are incorporated herein by reference, disclose various intravascular catheters/systems/methods for such purposes: U.S. Pat. Nos. 6,881,551 and 6,585,692 (tri-lobe catheter), U.S. Pat. Nos. 6,551,349 and 6,554,797 (metal catheter with bellows), U.S. Pat. Nos. 6,749,625 and 6,796,995 (catheters with non-straight, non-helical heat exchange elements), U.S. Pat. Nos. 6,126,684, 6,299,599, 6,368,304, and 6,338,727 (catheters with multiple heat exchange balloons), U.S. Pat. Nos. 6,146,411, 6,019,783, 6,581,403, 7,287,398, and 5,837,003 (heat exchange systems for catheter), U.S. Pat. No. 7,857,781 (various heat exchange catheters).

Present principles understand that accurately and constantly measuring patient core temperature for feedback purposes and, maximizing the rate of cooling for therapeutic purposes are among the challenges posed by intravascular temperature control. Accurate patient core temperature measurements can be provided by rectal probes, esophageal probes, bladder probes, and the like but such probes are uncomfortable for awake patients. Placing a sensor on the catheter itself in a vein of the patient avoids the need for an uncomfortable separate probe but since the catheter changes the temperature of the blood flowing past the catheter, to avoid the "thermal shadow" of the hot or cold catheter, cooling or heating of the patient periodically must be temporarily suspended long enough for the temperature of the blood near the sensor to stabilize at actual core body temperature. This undesirably prolongs cooling, for instance, when it is desired to cool the patient.

As to maximizing the rate of cooling, the larger the heat transfer area of the catheter, the faster it can cool, but size limits are reached even when using the entire inferior vena cava as a placement site. Existing catheters must accommodate the vein into which they are placed. With the above recognitions in mind, present principles are provided.

SUMMARY OF THE INVENTION

Accordingly, a transatrial intravascular temperature management catheter includes a lower heat exchange segment positionable in the inferior vena cava of a patient without blocking the inferior vena cava such that blood can flow past the lower heat exchange segment. The catheter also includes an upper heat exchange segment positionable in the superior vane cava of the patient without blocking the superior vena cava such that blood can flow past the upper heat exchange segment. Furthermore, the catheter includes a connecting segment connecting the heat exchange segments and positionable in the right atrium of the patient. Working fluid can be circulated through the heat exchange segments and the connecting segment to and from a heat exchange system external to the patient. The heat exchange system establishes a temperature of the working fluid at least in part based on a signal representing patient temperature. A temperature sensor on the distal tip of the upper heat exchange segment provides the signal representing patient temperature.

In some implementations, a heat exchange segment can be established by an elongated generally cylindrical balloon, or by a series of non-straight, non-helical links through which the working fluid flows serially from link to link. Or, a heat exchange segment can be established by a straight central supply tube surrounded by three helical return tubes. Yet again, a heat exchange segment can be established by alternating segments of bellows regions and helically fluted regions. If desired, the upper heat exchange segment may be smaller than the lower heat exchange segment in diameter and/or length. The connecting segment may be an elongated tube having a cylindrical outer surface throughout its length, and the connecting segment typically has a smaller diameter than either of the heat exchange segments.

In another aspect, a catheter includes a lower heat exchange segment positionable in the inferior vena cava of a patient without blocking the inferior vena cava such that blood can flow past the lower heat exchange segment. A connecting segment is connected to and extends away from the lower heat exchange segment and is positionable in the superior vena cava through the right atrium of the patient. The connecting segment resides in the superior vena cava when the lower heat exchange element is disposed in the inferior vena cava. Working fluid can be circulated through the heat exchange segment to and from a heat exchange system external to the patient. The heat exchange system establishes a temperature of the working fluid at least in part based on a signal representing patient temperature. A temperature sensor on the connecting segment provides the signal representing patient temperature.

In another aspect, a method includes advancing a catheter into a patient's inferior vena cava from a femoral insertion point, through the right atrium of the patient, and into the superior vena cava of the patient such that a heat exchange part of the catheter remains in the inferior vena catheter and a temperature sensing part of the catheter simultaneously resides in the superior vena cava. Working fluid is circulated through the heat exchange part to exchange heat with blood flowing past the heat exchange part in the inferior vena cava. The temperature of the working fluid is controlled responsive to signals from the temperature part. Alternatively, the catheter may be advanced into the patient from the opposite direction, i.e., from a neck insertion point such as the jugular vein or subclavian vein, through the superior vena cava, right atrium, and the inferior vend cava to end at a placement in which respective heat exchange parts are in the inferior and superior vena cavae and a connecting part between the heat exchange parts is in the right atrium.

The details of the present invention, both as to its structure and operation, can best be understood in reference to the

DETAILED DESCRIPTION OF THE PREFERRED EMBODIMENT

Figure 1:
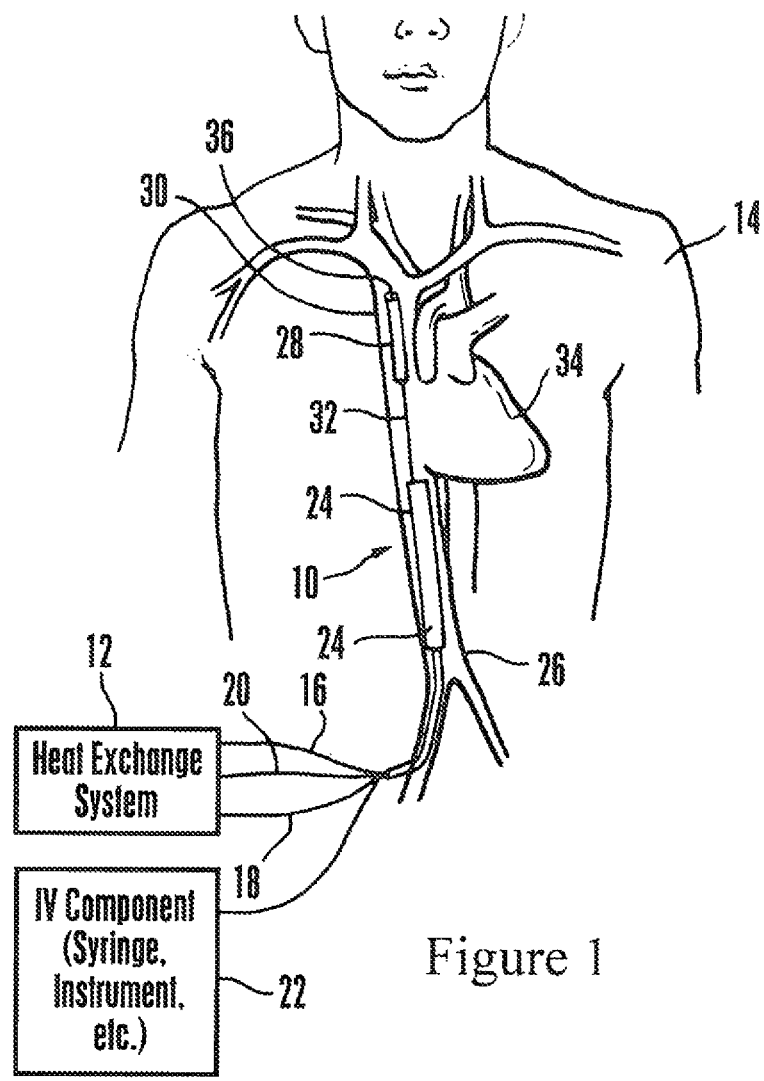
FIG. 1 is a schematic diagram showing the transatrial catheter advanced into both vena cavae with the connector portion of the catheter disposed in the right atrium.

Referring initially to FIG. 1, a transatrial intravascular temperature management, catheter 10 is in fluid communication with a catheter temperature control system 12 that includes a processor executing logic described in one or more of the patents referenced herein to control the temperature of working fluid circulating through the catheter 10 in accordance with a treatment paradigm responsive to patient core temperature feedback signals. In accordance with present principles, the catheter 10 can be used to induce therapeutic hypothermia in a patient 14 using the catheter, in which coolant such as but not limited to saline circulates in a closed loop, such that no coolant enters the body. Such treatment may be indicated for stroke, cardiac arrest (post-resuscitation), acute myocardial infarction, spinal injury, and traumatic brain injury. The catheter 10 can also be used to warm a patient, e.g., after bypass surgery or burn treatment, and to combat hyperthermia in, e.g., patient suffering from sub-arachnoid hemorrhage or intracerebral hemorrhage.

As shown, working fluid may be circulated between the heat exchange system 12 and catheter 10 through supply and return lines 16, 18 that connect to the proximal end of the catheter 10 as shown. Note that as used herein, "proximal" and "distal" in, reference to the catheter are relative to the system 12. A temperature signal from the below-described catheter-borne temperature sensor may be provided to the system 12 through an electrical line 20 or wirelessly if desired. The catheter 10, in addition to interior supply and return lumens through which the working fluid is circulated, may also have one or more infusion lumens connectable to an IV component 22 such as a syringe or IV bag for infusing medications into the patient, or an instrument such as an oxygen or pressure monitor for monitoring patient parameters, etc.

The catheter 10 includes a lower heat exchange segment 24 that is positionable through a femoral insertion point into the inferior vena cava 26 of the patient 14 without blocking the inferior vena cava 26 such that blood can flow past the lower heat exchange segment 24 as shown. Also, in some implementations the catheter 10 may include an upper heat exchange segment 28 that is positionable in the superior vane cava 30 of the patient without blocking the superior vena cava 30 such that blood can flow past the upper heat exchange segment 28. The upper heat exchange segment 28 can be smaller than the lower heat exchange segment 24 by virtue of having a smaller diameter than the lower heat exchange segment and/or by being shorter than the lower heat exchange segment. In any case, the upper heat exchange segment 28 is advanced first through the femoral insertion point, through the inferior vena cava and right ventricle, and into the superior vena cava, with the lower heat exchange segment 24 following and being disposed in the inferior vena cava once the upper heat exchange element 28 resides in the superior vena cava. Advancement may be over a guidewire or guide catheter and may be effected using fluoroscopy.

A connecting segment 32 connects the heat exchange segments 24, 28 and is positionable in the right atrium of the heart 34 of the patient. Working fluid is circulated through the heat exchange segments 24, 28 and the connecting segment 32 to and from the heat exchange system 12 external to the patient. Preferably, neither heat exchange segment 24, 28 extends into the atrium of the heart 34; only the connecting segment 32 is disposed in the heart. This is because the connecting segment, which can be a simple elongated thin cylindrical tube with only a supply and return lumen for the upper heat exchange segment 28 (and in some embodiments with one or more infusion lumens if desired), is smaller in diameter than the heat exchange segments 24, 28 so as to minimize the risk of contacting the heart muscle. Note that in some embodiments the upper heat exchange segment 28 may be omitted and the connecting segment 32 may be a very thin tube or even a wire that extends through the right atrium into the superior vena cava 30 for the sole purpose of bearing the below-described temperature sensor.

Indeed and with greater specificity, a temperature sensor 36 may be mounted on the distal tip of the upper heat exchange segment 28 to provide a signal representing patient temperature. Without limitation, the sensor 36 may be a thermistor, thermocouple, resistance temperature detector (RTD), or other suitable sensor. In any case, it will be appreciated that since blood in the superior vena cava flows toward the heart, the blood reaches the sensor 36 before it can be heated or cooled by the upper heat exchange segment 28. In other words, owing to the placement of the catheter 10 through the heart 34 with the sensor 36 in the superior vena cava, the sensor 36 is upstream of the "thermal shadow" of the heat exchange segment 28 and so provides an accurate indication of core body temperature.

Figure 2:
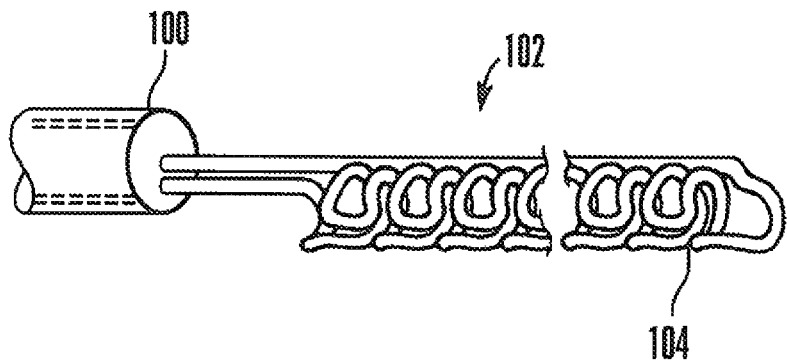
FIG. 2 is a perspective view of a first example catheter with a first example heat exchange member with plural non-straight, non-helical links, with portions of the heat exchange member broken away.

FIGS. 2-6 show example non-limiting embodiments of the lower heat exchange segment 24, it being understood that the same shapes may be used for the upper heat exchange segment 28. In FIG. 2 a catheter 100 has a heat exchange segment 102 established by a series of non-straight, non-helical links 104 through which the working fluid flows serially from link to link. Further details of the construction, and operation of the catheter 100 are set forth in the above-referenced U.S. Pat. No. 6,796,995.

Figure 3:
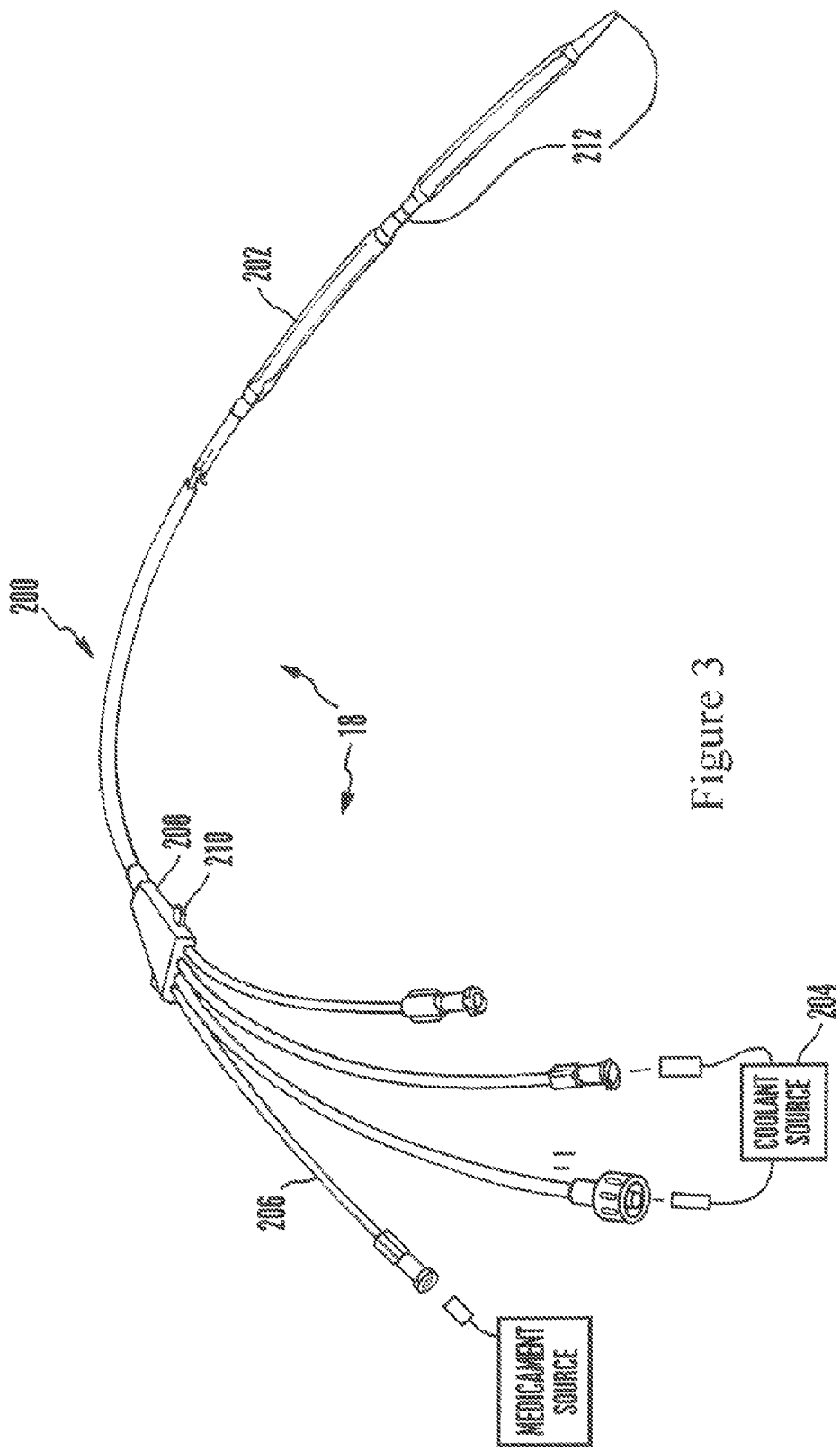
FIG. 3 is a perspective view of a second example catheter with second example heat exchange members configured as hollow balloons.

FIG. 3 shows a catheter 200 that has one or more axially-spaced cylindrical balloons 202 that carry circulating working fluid to and from a heat exchange system 204. The catheter 200 shown in FIG. 3 includes two additional infusion lumens connected to respective infusion tubes 206, with the various external tubes joining respective internal catheter lumens at a hub 208 which may be formed with suture wings 210 for suturing the hub 208 to the skin of the patient. The infusion lumens may terminate at respective axially-spaced infusion ports 212. Further details of the construction and operation of the catheter 100 are set forth in the above-referenced U.S. Pat. No. 6,368,304.

Figure 4:
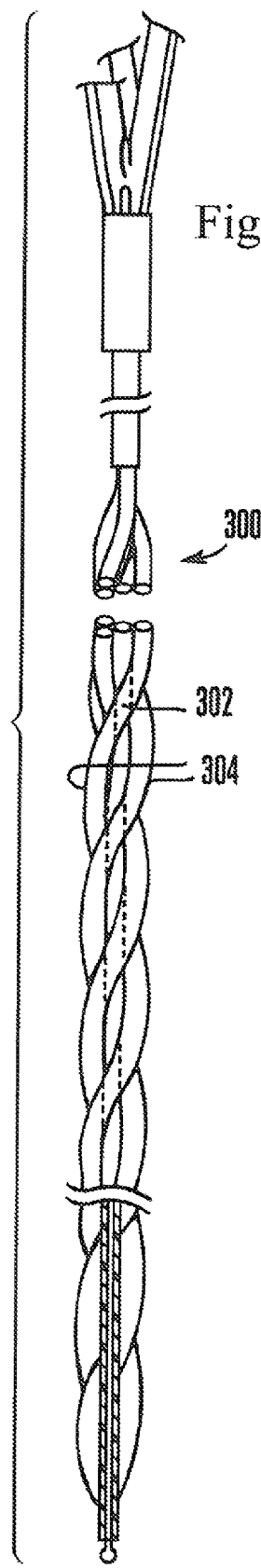
FIG. 4 is a side view of a third example catheter with a third example heat exchange member formed from a straight central supply tube surrounded by three helical return tubes.

Yet again, FIG. 4 shows a catheter 300 that has a straight central supply tube 302 surrounded by three helical return tubes 304. Further details of the construction and operation of the catheter 300 are set forth in the above-referenced U.S. Pat. Nos. 6,881,551 and 6,585,692.

Figure 5:
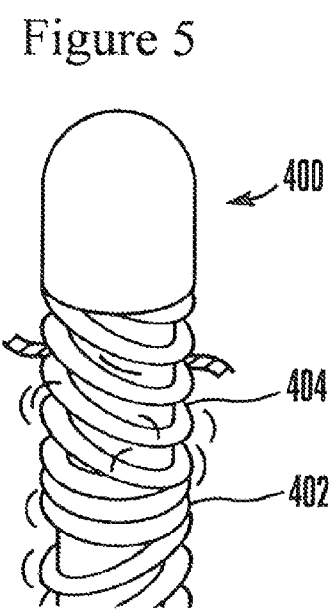
FIG. 5 is a perspective view of a fourth example catheter with fourth example heat exchange members that consist of alternating segments, along a metal tube, of bellows regions and fluted regions, with portions of the catheter broken away.
Figure 6:
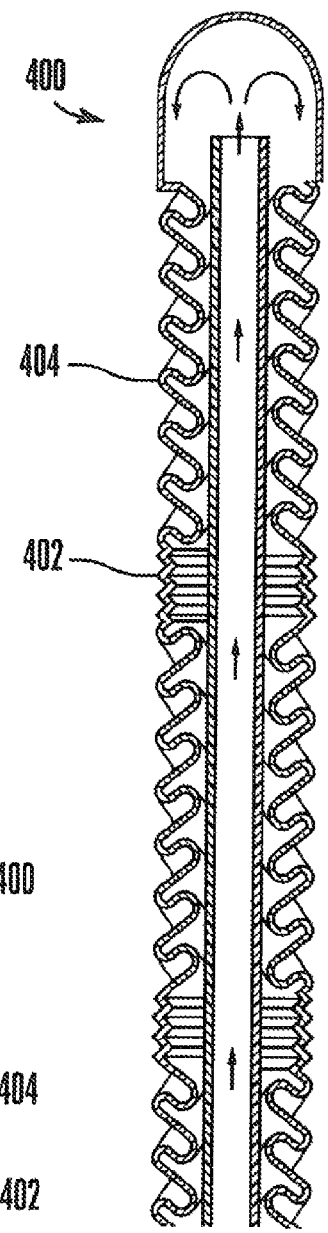
FIG. 6 is a cut-away view of the catheter shown in FIG. 5.

FIGS. 5 and 6 show a catheter 400 that may be made of a metal such as gold and that has alternating segments of bellows regions 402 and helically fluted regions 404. Further details of the construction and operation of the catheter 400 are set forth in the above-referenced U.S. Pat. Nos. 6,551,349 and 6,554,797.

While the particular TRANSATRIAL PATIENT TEMPERATURE CONTROL CATHETER is herein shown and described in detail, it is to be understood that the subject matter which is encompassed by the present invention is limited only by the claims.

What is claimed is:

1. A transatrial intravascular temperature management catheter, comprising:
    a lower heat exchange segment positionable in the inferior vena cava of a patient without blocking the inferior vena cava such that blood can flow past the lower heat exchange segment;
    an upper heat exchange segment positionable in the superior vane cava of the patient without blocking the superior vena cava such that blood can flow past the upper heat exchange segment when the lower heat exchange segment is located in the inferior vena cava;
    a connecting segment connecting the heat exchange segments and positionable in the right atrium of the patient when the lower heat exchange segment is located in the inferior vena cava and the upper heat exchange segment is positioned in the superior vena cava, working fluid being circulatable through the heat exchange segments and the connecting segment to and from a heat exchange system external to the patient, the heat exchange system establishing a temperature of the working fluid at least in part based on a signal representing patient temperature, the connecting segment being configured as a simple elongated thin cylindrical tube with a supply and a return lumen for the per heat exchange heat segment, the connecting segment having a smaller diameter than at least the lower heat exchange segment to minimize risk of the connecting segment contacting the right atrium; and
    a temperature sensor on the distal tip o the upper heat exchange segment providing the signal representing patient temperature.

2. The catheter of claim 1, wherein at least one heat exchange segment is established by an elongated generally cylindrical balloon.

3. The catheter of claim 1, wherein at least one heat exchange segment is established by a series of non-straight, non-helical links through which the working fluid flows serially from link to link.

4. The catheter of claim 1, wherein at least one heat exchange segment is established by a straight central supply tube surrounded by three helical return tubes.

5. The catheter of claim 1, wherein at least one heat exchange segment is established by alternating segments of bellows regions and fluted regions.

6. The catheter of claim 5, wherein the fluted regions have helical flutes.

7. The catheter of claim 1, wherein the upper heat exchange segment is smaller than the lower heat exchange segment.

8. The catheter of claim 7, wherein the upper heat exchange segment has a smaller diameter than the lower heat exchange segment.

9. The catheter of claim 7, wherein the upper he exchange segment is shorter than the lower beat exchange segment.

10. A catheter, comprising:
    a lower heat exchange segment positionable in the inferior vena cava of a patient without blocking the inferior vena cava such that blood can flow past the lower heat exchange segment;
    a connecting segment connected to and extending away from the lower heat exchange segment and positionable in the superior vena cava through the right atrium of the patient, the connecting segment residing in the superior vena cava when the lower heat exchange element is disposed in the inferior vena cave, working fluid being, circulatable through the heat exchange segment to and from a heat exchange system external to the patient, the heat exchange system establishing a temperature of the working fluid at least in part based on a signal representing patient temperature, the connecting segment being configured as a simple elongated thin cylindrical tube with a supply and a return lumen, the connecting segment having a smaller diameter than at least the lower heat exchange segment to minimize risk of the connecting segment contacting the right atrium; and
    a temperature sensor on the connecting segment providing the signal representing patient temperature.

11. The catheter of claim 10, wherein, at least one heat exchange segment is established by an elongated generally cylindrical balloon.

12. The catheter of claim 10, wherein at least one heat exchange segment is established by a series of non-straight, non-helical links through which the working fluid flows serially from link to link.

13. The catheter of claim 10, wherein at least one heat exchange segment is established by a straight central supply tube surrounded by three helical return tubes.

14. The catheter of claim 10, wherein at least one heat exchange segment is established by alternating segments of bellows regions and fluted regions.

15. The catheter of claim 14, wherein the fluted regions have helical flutes.

16. Method comprising:
    advancing a catheter into a patients inferior vena cava from a femoral insertion point, through the right atrium of the patient, and into the superior vena cava of the patient such that a heat exchange part of the catheter remains in the inferior vena cava and at least a temperature sensing part of the catheter simultaneously resides in the superior vena cava;
    circulating working fluid through the heat exchange part to exchange heat with blood flowing past the heat exchange part in the inferior vena cava; and
    controlling temperature of the working fluid responsive to signals from the temperature part.

17. The method of claim 16, wherein the heat exchange part in the inferior vena cava is a lower heat exchange part and the temperature sensing part also includes an upper heat exchange part distanced from the lower heat exchange part and fluidly connected thereto through the right atrium.

18. The method of claim 16, comprising controlling the temperature of the working fluid to lower core body temperature of the patient.

19. The method of claim 16, comprising controlling the temperature of the working fluid to raise core body temperature of the patient.

\* \* \* \* \*